(12) United States Patent
Gasparini et al.

(10) Patent No.: US 8,674,110 B2
(45) Date of Patent: Mar. 18, 2014

(54) PYRIDYLACETYLENES FOR USE AS RADIOTRACERS AND IMAGING AGENTS

(75) Inventors: Fabrizio Gasparini, Lausen (CH); Yves Auberson, Allschwil (CH); Lea Kessler, Zürich (CH); Simon Mensah Ametamey, Zürich (CH)

(73) Assignee: Novartis AG, Basel (CH)

( * ) Notice: Subject to any disclaimer, the term of this patent is extended or adjusted under 35 U.S.C. 154(b) by 999 days.

(21) Appl. No.: 10/573,162

(22) PCT Filed: Sep. 24, 2004

(86) PCT No.: PCT/EP2004/010743
§ 371 (c)(1),
(2), (4) Date: May 5, 2006

(87) PCT Pub. No.: WO2005/030723
PCT Pub. Date: Apr. 7, 2005

(65) Prior Publication Data
US 2009/0010838 A1    Jan. 8, 2009

(30) Foreign Application Priority Data
Sep. 26, 2003  (GB) .................................. 0322612.3

(51) Int. Cl.
*C07D 213/00*    (2006.01)

(52) U.S. Cl.
USPC ....................................................... 546/339

(58) Field of Classification Search
USPC .......................................... 546/338; 514/357
See application file for complete search history.

(56) References Cited

U.S. PATENT DOCUMENTS

2007/0265279 A1 * 11/2007 Gasparini et al. ......... 514/255.05

FOREIGN PATENT DOCUMENTS

| JP | 2000-351739 | 12/2000 |
| JP | 2002-087994 | 3/2002 |
| JP | 2003-508390 | 3/2003 |
| WO | 01/16121 | 3/2001 |
| WO | WO 0101621 | * 3/2001 |
| WO | WO 03/031452 | 3/2003 |
| WO | 2004/038374 | 5/2004 |

OTHER PUBLICATIONS

Patani et. al., "Bioisosterism: A Rational Approach in Drug Design", Chem. Rev. 1996, 96, 3147-3176.*
Hcaplus 2001:167983 Abstract, "Preparation of heterocyclic compounds as metabotropic glutamate receptor 5 (mGluR5) modulators", 2001, Cosford et. al.*
Patani et. al., "Bioisosterism: A Rational Approach in Drug Design", Chem. Rev. 1996, 3147-3176.*
Blake et. al., "Studies with Deuterated Drugs", Journal of Pharmaceutical Sciences, Mar. 1975, vol. 64, No. 3, pp. 367-391.*
Gasparini, et al., "3H-M-MPEP, a Potent, Subtype-Selective Radioligand for the Metabotropic Glutamate Receptor Subtype 5", Bioorg. Med. Chem. Lett., vol. 12, pp. 407-409 (2002).
Anderson, J.J., et al., In vivo receptor occupancy of mGlu5 receptor antagonists using the novel radioligand [3H] 3-methoxy-5-(pyridine-2-ylethynyl)pyridine). European Journal of Pharmacology, 473(1), pp. 35-40, 2003.
Cosford, Nicholas D.P. et al., [3H]-Methoxymethyl-MTEP and [3H]-Methoxy-PEPy: Potent and Selective Radioligands for the Metabotropic Glutamate Subtype 5 (mGlu5) Receptor, Bioorganic & Medicinal Chemistry Letters, Feb. 10, 2003, vol. 13, No. 3, pp. 351-354.

* cited by examiner

*Primary Examiner* — Janet L Andres
*Assistant Examiner* — Heidi Reese
(74) *Attorney, Agent, or Firm* — Jim Lynch

(57) ABSTRACT

The present invention relates to novel pyridylacetylene derivatives of formula I (I)

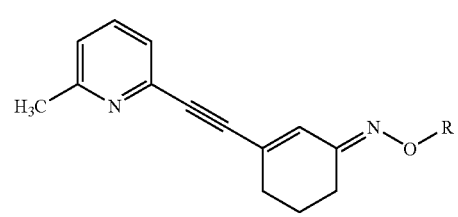

their preparation, their use as radio-traces/markers and compositions containing them.

2 Claims, No Drawings

PYRIDYLACETYLENES FOR USE AS RADIOTRACERS AND IMAGING AGENTS

The present invention relates to novel pyridylacetylene derivatives, their preparation, their use as radiotracers/markers and compositions containing them.

More particularly the invention provides a compound of formula I

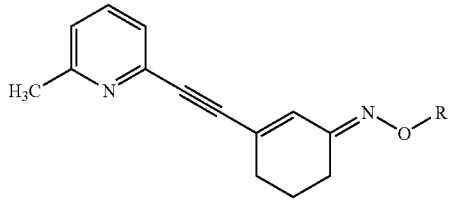

wherein
R is $CH_3$, $(CH_2)_nI$, $(CH_2)_nBr$ or $(CH_2)_nF$, n being 1, 2, 3 or 4
in free base or acid addition salt form.

Compounds of the formula I are preferred, wherein
R is $^{11}CH_3$, $(^3H)_3C$, $(CH_2)_n^{123}I$, $(CH_2)_n^{76}Br$ or $(CH_2)_n^{18}F$, n being 1, 2, 3 or 4
in free base or acid addition salt form.

In the case of possible stereoisomerism, e.g. cis/trans-isomerism of double bonds, the compounds can exist as pure stereoisomers or mixtures thereof.

In a further aspect, the invention provides a process for the production of the compounds of formula I and their salts, comprising the steps of
a) for the production of a compound of formula Ia

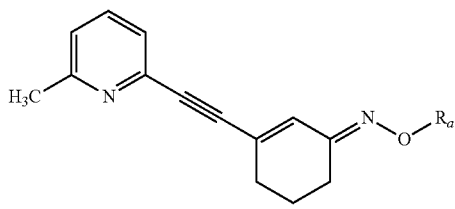

wherein $R_a$ is respectively $^{11}CH_3$ or $(^3H)_3C$, reacting the compound of formula II

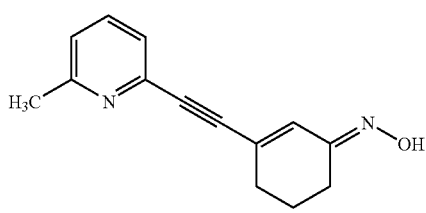

with respectively $^{11}CH_3I$ or $C(^3H)_3I$, in the presence of a base, or
b) for the production of a compound of formula Ib

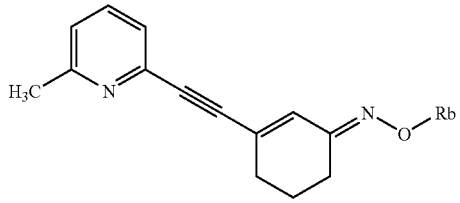

wherein Rb is respectively $(CH_2)_n^{18}F$, $(CH_2)_n^{123}I$ or $(CH_2)_n^{76}Br$, reacting a compound of formula III

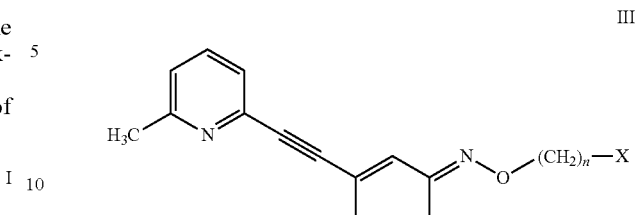

wherein n is as defined above and X is OTs or OMs, with respectively $^{18}F^\ominus$, $^{123}I^\ominus$ or $^{76}Br^\ominus$, or reacting the compound of formula II with a compound of formula IV $$X\text{—}Rb \qquad \qquad IV$$

wherein X and Rb are as defined above,
and recovering the resulting compound of formula I in free base form or in form of an acid addition salt.

The reactions can be effected according to known methods, for example as described in the Examples.

Working up the reaction mixtures and purification of the compounds thus obtained may be carried out in accordance to known procedures.

Acid addition salts may be produced from the free bases in known manner, and vice-versa.

The starting materials of formulae II, III and IV are known or may be obtained in analogous manner to know procedures, e.g. as described in the Examples.

Compounds of formula I in free base or acid addition salt form, hereinafter referred to as agents of the invention, exhibit valuable properties as histopathological labeling agents, imaging agents and/or biomarkers, hereinafter "markers", for the selective labeling of the metabotropic glutamate receptor subtype 5 (mGlu5 receptor).

More particularly the agents of the invention are useful as markers for labeling the central and peripheral mGlu5 receptors in vitro or in vivo (see Example 5-7).

The agents of the invention are therefore useful, for instance, for determining the levels of receptor occupancy of a drug acting at the mGlu5 receptor, or diagnostic purposes for diseases resulting from an imbalance or dysfunction of mGlu5 receptors, and for monitoring the effectiveness of pharmacotherapies of such diseases.

In accordance with the above, the present invention provides an agent of the invention for use as a marker for neuroimaging.

In a further aspect, the present invention provides a composition for labeling brain and peripheral nervous system structures involving mGlu5 receptors in vivo and in vitro comprising an agent of the invention.

In still a further aspect, the present invention provides a method for labeling brain and peripheral nervous system structures involving mGlu5 receptors in vitro or in vivo, which comprises contacting brain tissue with an agent of the invention.

The method of the invention may comprise a further step aimed at determining whether the agent of the invention labeled the target structure. Said further step may be effected by observing the target structure using positron emission tomography (PET) or single photon emission computed tomography (SPECT), or any device allowing detection of radioactive radiations.

The following examples illustrate the invention.

EXAMPLE 1

3-(6-Methyl-pyridin-2-ylethynyl)-cyclohex-2-enone O-[$^{11}$C-methyl]-oxime 3-(6-Methyl-pyridin-2-ylethynyl)-cyclohex-2-enone O-[$^{11}$C-methyl]-oxime is synthesized by reacting [$^{11}$C]-MeI with the sodium salt of 3-(6-methyl-pyridin-2-ylethynyl)-cyclohex-2-enone oxime (1 mg) in dry DMF (400 µl). [$^{11}$C]-MeI is introduced via a slow stream of helium and when addition is completed the reaction mixture is heated to 120° C. for 10 min. Product purification is accomplished by reversed phase HPLC using a C-18 µ-Bondapak column (7.8×300 mm) and a mobile phase consisting of CH$_3$CN/0.1% H$_3$PO$_4$ (70/30) at a flow rate of 5 ml/min. The retention time of the desired product is between 6 and 7 min. 3-(6-Methyl-pyridin-2-ylethynyl)-cyclohex-2-enone O-[$^{11}$C-methyl]-oxime is formulated in a solution containing polysorbatum (2%), ethanol (10%) and saline (0.9%). LogD=25 (determined using the classical shake-flask method).

The starting materials are prepared as described hereafter:
a) 3-(6-Methyl-pyridin-2-ylethynyl)-cyclohex-2-enone A solution of 2-ethynyl-6-methyl-pyridine (702 mg, 6 mmol), 3-bromo-cyclohex-2-enone (1.26 g, 7.2 mmol), bis-(triphenylphosphine)palladium-dichloride (168 mg, 0.24 mmol), copper(I) iodide (93 mg, 0.48 mmol), triethylamine (4.8 ml, 34.4 mmol) in 12 ml DMF is heated to 55° C. for 1 h. After that time the solution is diluted with ethyl acetate (500 ml) and washed with sat aq. NaHCO$_3$ (1×150 ml). The water phase is extracted with ethyl acetate (1×150 ml) and the combined organic phases are dried over Na$_2$SO$_4$, filtered and concentrated in vacuo. The residue (1.88 g) is purified on column chromatography (silica gel, eluent hexane/ethyl acetate 3:1 v/v) and the fractions containing the desired compound are collected and concentrated in vacuo to yield 1.05 g (yield=82%) of the title compound as a light yellow oil.
b) 3-(6-Methyl-pyridin-2-ylethynyl)-cyclohex-2-enone oxime A solution of 3-(6-methyl-pyridin-2-ylethynyl)-cyclohex-2-enone (422 mg, 2 mmol) and hydroxylamine hydrochloride (278 mg, 4 mmol) in pyridine (20 ml) is stirred for 17 h at RT. After that time the solvent is evaporated in vacuo. The residue is dissolved in ethyl acetate (300 ml) and washed with sat NaHCO$_3$ (1×50 ml). The water phase is extracted with ethyl acetate (1×50 ml). The combined organic phases are dried over Na$_2$SO$_4$, filtered and concentrated in vacuo. The residue (0.45 g) is purified on column chromatography (Silica gel, eluent hexane/ethyl acetate 2:1 v/v) and the fractions containing the desired compound are collected and concentrated in vacuo to yield 0.192 g (yield=42%) of the title compound as light yellow crystals, m.p. 166-168° C.

EXAMPLE 2

3-(6-Methyl-pyridin-2-ylethynyl)-cyclohex-2-enone O-[tri($^3$H)-methyl]-oxime

The title compound can be prepared by reacting 3-(6-methyl-pyridin-2-ylethynyl)-cyclohex-2-enone oxime with [$^3$H]-MeI (0.5 equivalent) in the presence of K$_2$CO$_3$ in DMF at 100° C. for 180 min, followed by a purification by reversed phase chromatography.

EXAMPLE 3

3-(6-Methyl-pyridin-2-ylethynyl)-cyclohex-2-enone O-(2-[$^{18}$F-fluoro]-ethyl)-oxime The sodium salt of the 3-(6-methyl-pyridin-2-ylethynyl)-cyclohex-2-enone oxime (2 mg) is reacted in dry DMF (400 µl) with [$^{18}$F]-2-fluoro-ethyltosylate (obtained from ethyleneditosylate and [$^{18}$F]-KF-Kryptofix complex) at 100° C. for 10 min. The reaction mixture is purified through a tC-18 Sep-Pak cartridge, and the fractions containing the desired product are further purified by a semi-preparative reversed phase HPLC using a C18 Bondclone column (300×7.8 mm) and a mobile phase consisting of CH$_3$CN/0.01 M H$_3$PO$_4$ (70/30) at a flow rate of 4 ml/min. The fraction containing the product (retention time between 12 and 13 min) is passed through a tC-18 Sep-Pak cartridge and eluted with 1 ml of ethanol. This ethanolic solution is buffered with 0.15M phosphate buffer to give after sterile filtration an isotonic and injectable solution.

EXAMPLE 4

3-(6-Methyl-pyridin-2-ylethynyl)-cyclohex-2-enone O-[$^{18}$F-fluoro]-methyl)-oxime The sodium salt of the 3-(6-methyl-pyridin-2-ylethynyl)-cyclohex-2-enone oxime (2 mg) is reacted in dry DMF (400 µl) with [$^{18}$F]CH$_2$OTf at 100° C. for 30 min. After an initial purification by passing the reaction mixture through a tC-18 Sep-Pak cartridge, 3-(6-methyl-pyridin-2-ylethynyl)-cyclohex-2-enone O-[$^{18}$F-fluoro]-methyl-oxime was finally purified by a semi-preparative reversed phase HPLC using a C18 Bondclone column (300×7.8 mm) and a mobile phase consisting of CH$_3$CN/0.01 M H$_3$PO$_4$ (70/30) at a flow rate of 4 ml/min. The product is formulated in analogy to 3-(6-methyl-pyridin-2-ylethynyl)-cyclohex-2-enone O-(2-[18F-fluoro]-ethyl)-oxime (example 3).

EXAMPLE 5

$K_i$/$IC_{50}$ determination (binding assay)

In vitro, the affinity for the mGlu5 receptor is determined using a radioligand displacement technique as described by Gasparini et al, Biorg. Med. Chem. Lett. 2002, 12, 407-409. 3-(6-methyl-pyridin-2-ylethynyl)-cyclohex-2-enone O-methyl-oxime shows an $IC_{50}$ of 8 nM (Hill coefficient 1.08; 95% confidence intervals: 6.0-10.0 nM) for the displacement of [3H]-2-methyl-6-((3-methoxyphenyl)ethynyl)-pyridine from membrane of L-tk cells stably expressing the human mGlu5 receptor (Daggett et al, Neuropharm. 1995, 34:871-886). Using the Cheng-Prusoff equation, a $K_i$ of 4 nM is calculated (radioligand concentration used for the assay: 2 nM).

EXAMPLE 6

Organ and Brain Structure Distribution

Two groups of male adult Sprague-Dawley rats weighing 250-300 g are used for the biodistribution studies. The first group (n=3) serves as the control group and the second group (n=3) serves as the blockade group. Each animal received 250-300 pmol (0.6-40 MBq) of 3-(6-methyl-pyridin-2-ylethynyl)-cyclohex-2-enone O-[$^{11}$C-methyl]oxime via a lateral tail vein. The blockade group is co-injected with 2-methyl-6-((3-methoxyphenyl)ethynyl)-pyridine (1 mg/kg) whereas the control group (n=3) receives a corresponding volume of 0.9% NaCl. The animals are sacrificed 30 min post-injection. Organ or brain regions such as hippocampus, striatum, cortex and cerebellum are removed and measured in a gamma-counter. The tissue distribution is expressed as percentage of injected dose per gram wet tissue (% ID/g organ).

EXAMPLE 7

Results of the Brain Distribution Study with 3-(6-methyl-pyridin-2-ylethynyl)-cyclohex-2-enone O-[$^{11}$C-methyl]-oxime The table below displays the percentage of the injected dose normalized per gram of tissue. K1, K2, K3 are individual values for control animals. B1, B2, B3 are individual values for animals co-injected with 2-methyl-6-((3-methoxyphenyl)ethynyl)-pyridine.

| Organ | K1 | K2 | K3 | B1 | B2 | B3 |
|---|---|---|---|---|---|---|
| Hippocampus | 0.16154 | 0.25440 | 0.21264 | 0.05184 | 0.06195 | 0.05972 |
| Striatum | 0.22564 | 0.30685 | 0.28164 | 0.06495 | 0.07158 | 0.06487 |
| Cortex | 0.14849 | 0.18316 | 0.16909 | 0.04964 | 0.05582 | 0.05431 |
| Cerebellum | 0.03322 | 0.03925 | 0.03699 | 0.04052 | 0.03608 | 0.03421 |
| Midbrain | 0.07703 | 0.10559 | 0.09091 | 0.03876 | 0.04700 | 0.04422 |
| Restbrain | 0.05519 | 0.06520 | 0.06070 | 0.03832 | 0.04762 | 0.04383 |
| Whole brain | 0.11123 | 0.13659 | 0.12999 | 0.04580 | 0.05118 | 0.04951 |

The invention claimed is:

1. A process for the production of a compound of formula I

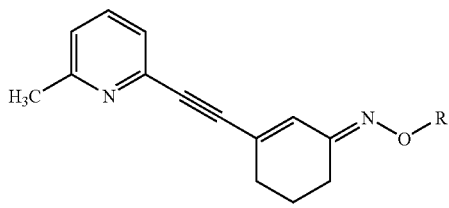

wherein R is $^{11}CH_3$, $C(^3H)_3$, $(CH_2)_n$-$^{18}$F, n being 1, 2,,3, or 4, in free base or an acid addition salt thereof, comprising the steps of a) for the production of a compound of formula Ia

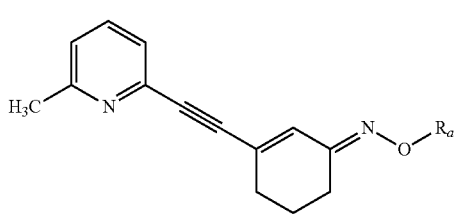

wherein $R_a$ is, respectively, $^{11}CH_3$ or $C(^3H)_3$, reacting a compound of formula II

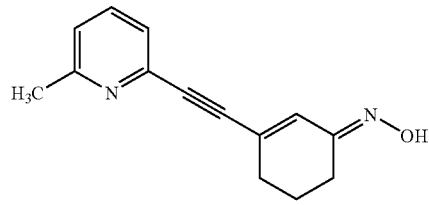

with, respectively, $^{11}CH_3I$ or $C(^3H)_3I$, in the presence of a base; or b) for the production of a compound of formula Ib

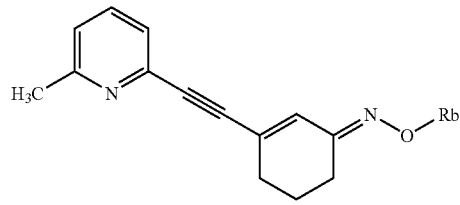

wherein Rb is, respectively, $(CH_2)_n$-$^{18}$F, $(CH_2)_n$-$^{123}$I, or $(CH_2)_n$-$^{76}$Br, reacting a compound of formula III

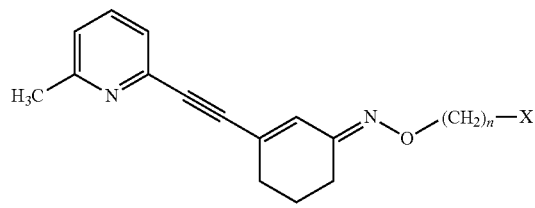

wherein n is as defined above and X is OTs or OMs, with, respectively, $^{18}F^-$, $^{123}I^-$ or $^{76}Br^-$ or, reacting the compound of formula II with a compound of formula X- Rb, wherein X and Rb are as defined above, and recovering the resulting compound of formula I in free base form or in the form of an acid addition salt.

2. A method for determining the levels of receptor occupancy of a drug acting at the mGluR5 receptors in one or more of the hippocampus, striatum, cortex and cerebellum regions of the brain, comprising contacting brain tissue from said brain region or regions with a composition comprising a compound formula I

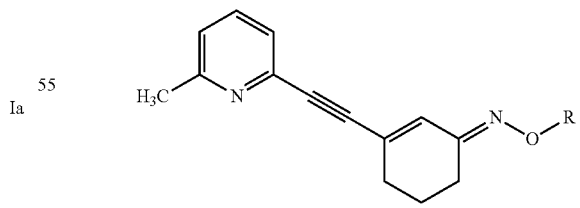

wherein R is $^{11}CH_3$, $C(^3H)_3$, $(CH_2)_n$-$^{123}$I, $(CH_2)_n$-$^{76}$Br, or $(CH_2)_n$-$^{18}$F, n being 1, 2,,3, or 4, in free base or an acid addition salt form, and measuring the tissue distribution of labeled mGluR5 receptors in said brain region or regions using a device capable of detecting radioactive emissions.

* * * * *